(12) United States Patent
Hefny

(10) Patent No.: US 8,882,988 B2
(45) Date of Patent: Nov. 11, 2014

(54) POTENTIOMETRIC DEVICE AND METHOD SELECTIVE FOR PIOGLITAZONE

(71) Applicant: UMM Al-Qura University, Makkah (SA)

(72) Inventor: Amr Lotfy Saber Hefny, Makkah (SA)

(73) Assignee: UMM Al-Qura University, Makkah (SA)

( * ) Notice: Subject to any disclaimer, the term of this patent is extended or adjusted under 35 U.S.C. 154(b) by 133 days.

(21) Appl. No.: 13/727,543

(22) Filed: Dec. 26, 2012

(65) Prior Publication Data

US 2014/0174952 A1 Jun. 26, 2014

(51) Int. Cl.
*G01N 27/333* (2006.01)

(52) U.S. Cl.
CPC .................................. *G01N 27/3335* (2013.01)
USPC ..................... 205/780.5; 514/342; 549/281.7; 422/68.1; 422/82.01; 435/287.1

(58) Field of Classification Search
CPC .................................................. G01N 27/3335
USPC ......... 205/780.5; 422/68.1, 82.01; 435/287.1; 549/281.7; 514/342
See application file for complete search history.

(56) References Cited

U.S. PATENT DOCUMENTS

| 3,926,734 | A | 12/1975 | Gray et al. |
| 4,618,587 | A | 10/1986 | Premoli et al. |
| 2001/0051109 | A1 | 12/2001 | Anderson et al. |

OTHER PUBLICATIONS

Shrotri et al., IJPBS |vol. 2| Issue 1 |Jan.-Mar. |2012|211-217.*
G.A.E. Mostafa, A. Al-Majed / Journal of Pharmaceutical and Biomedical Analysis 48 (2008) 57-61.*
Saber et al., Int. J. Electrochem. Sci., 9 (2014) 4374-4383.*
Amr L. Saber, "Determination of Pioglitazone Hydrochloride in Tablets by High-Performance Liquid Chromatography", Pak. J.Anal. Environ. Chem. vol. 9, No. 2 (2008), pp. 118-121.
Faridbod et al., "Potentiometric Sensor for Quantitative Analysis of Pioglitazone Hydrochloride in Tablets Based on Theoretical Studies", *International Journal of Electrochemical Science*, (2010) 890-894.
Amr L. Saber, "Novel Potentiometric Sensors for Determination of Melatonin and Oxomemazine in Biological Samples and in Pharmaceutical Formulations", *Electroanalysis*, vol. 22, Issue 24, pp. 2997-3002, Dec. 2010.
Kamran Abro, Najma Memon, M.I. Bhanger, S.A. Mahesar and Shahnaz Perveen, "Liquid Chromatographic Determination of Pioglitazone in Pharmaceuticals, Serum and Urine Samples", *Pak. J. Anal. Environ. Chem.* vol. 12, No. 1 & 2 (2011) 49-54.
C.H. Ravikanth, A. Anil Kumar, V. Uday Kiran, S. Prashanth, B. Madhu, and Y. Narsimha Reddy, "Sensitive and Rapid HPLC Method for the Determination of Pioglitazone in Rat Serum", *International Journal of Pharmaceutical Sciences and Drug Research* 2011; 3(1): 38-41.

* cited by examiner

*Primary Examiner* — Jennifer Dieterle
(74) *Attorney, Agent, or Firm* — Richard C. Litman

(57) ABSTRACT

The potentiometric device and method selective for pioglitazone relates to the detection of pioglitazone in urine, in other liquid biological samples, and in pharmaceutical preparations for quality control testing and the like, and particularly to the use of a potentiometric sensor for potentiometric detection and measurement of the concentration of pioglitazone. The potentiometric sensor includes a plasticized polyvinyl chloride (PVC) matrix membrane having an ionophore impregnated or embedded therein. The ionophore is an iodobismuth anion in which the iodobismuth anion forms a complex with pioglitazone. The polymer membrane is plasticized with either ortho-nitrophenyl octyl ether (NPOE) or dioctyl phthalate (DOP).

13 Claims, No Drawings

POTENTIOMETRIC DEVICE AND METHOD SELECTIVE FOR PIOGLITAZONE

BACKGROUND OF THE INVENTION

1. Field of the Invention

The present invention relates to the qualitative and quantitative chemical analysis of drugs, particularly to a potentiometric device and method selective for pioglitazone that may be used detection and measurement of the concentration of the drug for quality control in the manufacture of the drug, etc.

2. Description of the Related Art

A potentiometric sensor is a type of electrochemical sensor that may be used to determine the presence and concentration of substances in a gas or solution. These sensors measure the electrical potential of an electrode when no current is flowing. The signal is measured as the potential difference (voltage) between the working electrode and the reference electrode. The working electrode's potential must depend on the concentration of the analyte in the gas or solution phase. The reference electrode is needed to provide a defined reference potential.

Potentiometric sensors typically use an ion selective electrode (ISE). The voltage between a reference electrode and the ISE exposed to an analyte solution can be measured, and since this voltage is related to the activity of the analyte by the Nernst equation, the unknown concentration of the analyte can be computed. There are several different types and configurations of ion selective electrodes, with and without internal reference solutions. The ISE usually uses a semipermeable membrane or selectively permeable membrane that is selective for the cation or anion of interest. One type of membrane used in an ion selective electrode is a polymer membrane. The polymer membrane includes a polymer matrix, often of poly (vinyl chloride) (PVC), that is doped with an ionophore (an organic ion exchange agent). The membrane also may include a plasticizer to keep the polymer soft and amorphous so that the ion of interest can be transported between the aqueous analyte solution and the ionophore embedded in the polymer matrix. The plasticizer may also affect the dielectric constant of the polymer membrane. Plasticized polymers used for ISE membranes are sometimes described as viscous liquids and referred to in the literature as liquid membranes.

One type of ionophore used in an ISE is an ion-pair ionophore. The potential measured by an ion-pair sensor electrode is dependent upon the relative attraction and repulsion forces of the ion-pair complex and the ionic species of the analyte of interest. Pioglitazone ([(±)-5-[[4-[2-(5-ethyl-2-yridinyl) ethoxy]phenyl]methyl]-2,4-]thiazolidinedione) hydrochloride is an oral anti-hyperglycemic agent that is used in the treatment of type 2 diabetes. A testing method that is quick, simple, and relatively inexpensive for detecting and measuring the concentration of pioglitazone in pharmaceutical manufacture and in biological fluids for ensuring therapeutic levels of the unmetabolized drug is desirable.

Thus, a potentiometric device and method selective for pioglitazone solving the aforementioned problems is desired.

SUMMARY OF THE INVENTION

The potentiometric device and method selective for pioglitazone relates to the detection of pioglitazone in urine, in other liquid biological samples, and in pharmaceutical preparations for quality control testing and the like, and particularly to the use of a potentiometric sensor for potentiometric detection and measurement of the concentration of pioglitazone. The potentiometric sensor includes a plasticized polyvinyl chloride (PVC) matrix membrane having an ionophore impregnated or embedded therein. The ionophore is an iodobismuth anion in which the iodobismuth anion forms a complex with pioglitazone. The polymer membrane is plasticized with either ortho-nitrophenyl octyl ether (NPOE) or dioctyl phthalate (DOP).

These and other features of the present invention will become readily apparent upon further review of the following specification.

DETAILED DESCRIPTION OF THE PREFERRED EMBODIMENTS

The potentiometric device and method selective for pioglitazone relates to the detection of pioglitazone in urine, in other liquid biological samples, and in pharmaceutical preparations for quality control testing and the like, and particularly to the use of a potentiometric sensor for potentiometric detection and measurement of the concentration of pioglitazone. The potentiometric sensor includes a plasticized polyvinyl chloride (PVC) matrix membrane having an ionophore impregnated or embedded therein. The ionophore is an iodobismuth anion in which the iodobismuth anion forms a complex with pioglitazone. The polymer membrane is plasticized with either ortho-nitrophenyl octyl ether (NPOE) or dioctyl phthalate (DOP).

In a representative example, the ionophore is made by adding 2 mL of 0.006 M $BiI_3$ (bismuth triiodide) to 4 mL of 0.006 M NaI (sodium iodide) to form an iodobismuth anion. Then, 7.2 mL of 0.005 M concentration pioglitazone is added, forming a solid ion-pair complex that precipitates. By way of further example, 40 mg of the bismuth iodate-pioglitazone precipitate just described was combined with 360 mg of ortho-nitrophenyl octyl ether (or 360 mg of dioctyl phthalate) and 170 mg of poly (vinyl chloride) to form a plasticized polymer membrane suitable for use in an ion selective membrane (ISE) in a potentiometric sensor.

The sensor is preferably conditioned by soaking in 0.1 mol/L pioglitazone solution for at least two days prior to use, and then is stored in the same solution.

The sensor was then calibrated against known standards to determine the range of the sensor, and tested to determine the effect of pH and the selectivity of the polymer membrane in the presence of interfering cations. The electrode is found to have a Nemstian response to pioglitazone in a concentration range between approximately $1.0 \times 10^{-9}$ and $1.0 \times 10^{-1}$ mol/L in a pH range of between 3.0 and 7.0. The working electrode is found to show good discrimination toward pioglitazone with respect to most common cations.

It is to be understood that the present invention is not limited to the embodiments described above, but encompasses any and all embodiments within the scope of the following claims.

I claim:

1. A potentiometric method selective for pioglitazone, comprising the steps of:
    at least partially filling a cell with a solution to be tested;
    at least partially immersing an ion selective electrode in the solution, the ion selective electrode having a plasticized polymer membrane doped with an ionophore, the ionophore being an ion-pair complex consisting of an iodobismuth-pioglitazone complex;
    measuring electrical potential between the ion selective electrode and a reference electrode; and comparing the measured potential with a calibration curve of the ion selective membrane to detect the presence of pioglitazone in the solution and determine the concentration thereof.

2. The potentiometric method selective for pioglitazone as recited in claim 1, wherein said polymer membrane comprises poly (vinyl chloride).

3. The potentiometric method selective for pioglitazone as recited in claim 2, wherein said plasticizer comprises ortho-nitrophenyl octyl ether (NPOE).

4. The potentiometric method selective for pioglitazone as recited in claim 2, wherein said plasticizer comprises dioctyl phthalate (DOP).

5. The potentiometric method selective for pioglitazone as recited in claim 1, wherein the test solution comprises a biological sample.

6. The potentiometric method selective for pioglitazone as recited in claim 1, wherein the test solution comprises urine.

7. The potentiometric method selective for pioglitazone as recited in claim 1, wherein the test solution comprises a pharmaceutical sample of pioglitazone.

8. A polymer membrane selective for pioglitazone, comprising a membrane formed from a polymer doped with an ion-pair complex consisting of an iodobismuth-pioglitazone complex.

9. The polymer membrane according to claim 8, further comprising a plasticizer mixed with the polymer.

10. The polymer membrane according to claim 9, wherein said plasticizer comprises dioctyl phthalate (DOP).

11. The polymer membrane according to claim 9, wherein said plasticizer comprises o-nitrophenyl octyl ether (o-NPOE).

12. The polymer membrane according to claim 9, wherein said polymer comprises poly (vinyl chloride).

13. An ionophore selective for pioglitazone, consisting of a drug ion-pair complex, the ion-pair complex being an ion-pair complex consisting of an iodobismuth-pioglitazone complex.

* * * * *